United States Patent [19]

Gelboin et al.

[11] Patent Number: 5,506,138
[45] Date of Patent: Apr. 9, 1996

[54] RECOMBINANT VACCINIA VIRUS ENCODING CYTOCHROMES P-450

[75] Inventors: Harry V. Gelboin, Chevy Chase; Narayana Battula, Rockville; Frank J. Gonzalez; Bernard Moss, both of Bethesda, all of Md.

[73] Assignee: The United States of America as represented by the Secretary of the Department of Health and Human Services, Washington, D.C.

[21] Appl. No.: 166,287

[22] Filed: Dec. 13, 1993

Related U.S. Application Data

[60] Continuation of Ser. No. 930,781, Aug. 17, 1992, abandoned, which is a division of Ser. No. 787,777, Nov. 6, 1991, Pat. No. 5,164,313, which is a continuation of Ser. No. 58,387, Jun. 5, 1987, abandoned.

[51] Int. Cl.[6] .......................... C12N 9/02; C12N 15/53; C12N 15/85; C12N 15/86
[52] U.S. Cl. .................. 435/252.3; 435/189; 435/240.2; 536/23.2; 935/32; 935/60; 935/70
[58] Field of Search ................................ 435/69.1, 172.3, 435/189, 190, 252.3, 320.1; 536/23.2

[56] References Cited

U.S. PATENT DOCUMENTS 4,766,068  8/1988  Oeda et al. ............................... 435/68
5,164,313  11/1992  Gelboin et al. ......................... 435/189

FOREIGN PATENT DOCUMENTS 236485  4/1986  Japan ......................................... 435/189

OTHER PUBLICATIONS

Moss, B., Poxviridae and Their Replication, Virology, Second Edition (1990) pp. 2079–2111.
Dathu, G. S. et al. 1983 Biol. Abstr. vol 76, p. 8080 Abstract 73560.
Ghezzi, P. et al. 1985. Biological Abstracts, vol. 80, p. AB–961, abstract 91194.
Stephens, E. B. et al 1986 Biological Abstracts, vol. 81 p. AB–560, abstract 112680.
Zuber et al., Science, vol. 234, pp. 1258–1261, Dec., 1986; "Expression of Bovine 17α–Hydroxylase Cytochrome P–450 cDNA . . . ".
Mackett, M., and Smith, G. L., 1986, Journal of General Virology, 67(10): 2067–2082.
Stephens, E. B., et al. 1986, The EMBO Journal, 5(2): 237–245.
Ghezzi, P., et al. 1985, Cancer Research, 45(8): 3444–3447.
Sadano, H., et al., 1985, The Journal of Biochemistry, 98(4):1321–1331.
Bock, K. W., et al., 1970, Biochemical and Biophysical Research Communications, 41(2):374–380.
Garner, R. C., et al., 1969, Biochemical and Biophysical Research Communications, 37(6):883–887.
Grayzel, A. I., et al., 1967, Biochemical and Biophysical Research Communications, 28(5):705–710.
Murakami, H., et al., 1986, DNA, 5(1): 1–10.
Zuber, M. X., et al., 1986, Science, 234.
Battula, N., et al., 1987, Proceedings of the National Academy of Sciences, U.S.A., 84: 4073–4077.
Chakabarti, S., et al., 1985, Molecular and Cellular Biology 5(12):3403–3409.
Wickner, W. T., et al., 1985, Science, 230(4724):400–407.
Dathu, G. S., et al., 1983, Cancer Letters, 18(3):237–243.
Negishi, M., and Nebert, P. W., 1979, The Journal of Biological Chemistry, 254(21): 11015–11023.
Kimura, S., et al., 1984, The Journal of Biological Chemistry, 259(17):10705–10713.
Gonzalez, F. J., et al., Gene, 29: 281–292.
Oeda, K., et al., 1985, DNA 4(3): 203–210.
Gelboin, H. V., and Friedman, F. K., 1985, Biochemical Pharmacology, 34(13): 2225–2234.

*Primary Examiner*—Robert A. Wax
*Assistant Examiner*—William W. Moore
*Attorney, Agent, or Firm*—Morgan & Finnegan

[57] ABSTRACT

The present invention is related to the construction and application of vaccinia virus containing DNA sequences for encoding and efficient expression of enzymatically active cytochrome P-450 polypeptides in mammalian cells. Preparation and use of pure P1-450 and P3-450 cytochromes have been described.

9 Claims, 6 Drawing Sheets

RECOMBINANT VACCINIA VIRUS ENCODING CYTOCHROMES P-450

This is a continuation of U.S. application Ser. No. 07/930,781, filed Aug. 17, 1992, now abandoned, which is a divisional of U.S. application Ser. No. 787,777, filed Nov. 6, 1991, now U.S. Pat. No. 5,164,313, issued Nov. 17, 1992, which is a continuation of U.S. application Ser. No. 058,387, filed Jun. 5, 1987, now abandoned.

BACKGROUND OF THE INVENTION

The present invention is related to the construction and application of recombinant vaccinia virus containing DNA sequences for encoding and efficient expression of enzymatically active cytochromes P-450 in mammalian cells.

The cytochromes P-450 are a large family of hemoproteins capable of metabolizing xenobiotics such as drugs, carcinogens and environmental pollutants as well as endobiotics such as steroids, fatty acids and prostaglandins. Some members of the cytochrome P-450 family are inducible in both animals and cultured cells while other constitutive forms are non-inducible. This group of enzymes carry out beneficial metabolic activities by detoxification of xenobiotics as well as harmful metabolic conversion of xenobiotics to toxic, mutagenic and carcinogenic forms (Gelboin, Physiol.Rev. 60:1107–1166, 1980).

In animals, multiple molecular forms of cytochrome P-450s are expressed simultaneously and they all exhibit common physical and biological properties. The multiplicity and common properties of the cytochromes P-450 make it difficult to separate different forms of cytochrome P-450 especially the minor forms. And even where P-450 cytochromes may have been obtained perhaps in purified form by conventional enzyme purification procedures, they were obtained out of the natural biological membrane association and all such preparations require the addition of NADPH-cytochrome P-450 reductase and other cell fractions for enzymatic activity. These factors have prevented a clearer understanding of the role and function of individual forms of cytochrome P-450 in metabolism, detoxification and activation of both xenobiotic and endobiotic substrates. Recent reports on the expression of cloned P-450 DNA sequences by DNA transfection are limited to yeast and COS 1 monkey helper cells (Oeda et al, and Zuber et al, DNA, 4:203,210, 1985; Science 234:1258–1261, 1986). However, no expression of functional cytochrome P-450 has been reported in mammalian systems of wide host range using infectious viruses.

SUMMARY OF THE INVENTION

It is, therefore, an object of the present invention to construct infectious recombinant vaccinia viruses containing full-length cDNA sequences for cytochromes P1-450 and P3-450.

It is a further object of the present invention to provide a system which expresses enzymatically active P1-450 and P3-450 proteins in a variety of mammalian cells including human cells.

It is another object of the present invention to provide functionally intact, P1-450 and P3-450 pure polypeptides without requiring the extraneous addition of NADPH cytochrome P450 reductase for enzymatic activity.

It is a still further object of the present invention to provide a method for expressing cytochrome P-450 from different sources including those from humans for expression and defining substrate and product specificity.

Various other objects and advantages of the present invention will become apparent from the Detailed Description of the Invention.

BRIEF DESCRIPTION OF THE DRAWINGS

These and other objects, features and many of the attendant advantages of the invention will be better understood upon a reading of the following detailed description when considered in connection with the accompanying drawings wherein:

FIG. 2 demonstrates identification of cytochrome P1-450 and P3-450 polypeptides. Lysates (100 µg) were electrophoresed and detected by immunoblotting. Stained protein molecular weight markers are shown on the right. 2A. Expression in WI-38 and NIH 3T3 cells. 2B. Time course of synthesis in NIH 3T3 cells. The minor $M_r$=80,000 band detected in all cell lanes was not detected when diluted antisera was used;

DETAILED DESCRIPTION OF THE INVENTION

The above and various other objects and advantages of the present invention are achieved by (a) constructing recombinant infectious vaccinia viruses containing cDNA sequences for encoding cytochrome P-450 polypeptides so that mammalian cells when infected with said recombinant viruses efficiently express the P-450 polypeptides; and (b) providing functionally intact, pure P1-450 and P3-450 polypeptides without requiring the extraneous addition of NADPH cytochrome P450 reductase for enzymatic activity.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

The term "pure" as used herein refers to the individual cytochrome P-450 enzyme only, with no detectable background for any other P-450 enzyme in the uninfected control cells or in cells infected with wild type vaccinia virus.

MATERIALS AND METHODS

Enzymes and Chemicals: Restriction endonuclease, DNA polymerase 1 and its Klenow fragment, and T4 DNA ligase were purchased from commercial sources and used according to the manufacturers specifications. 5-Bromo-4-Chloro-3-Indolyl-β-D-glactosidase (X-gal) was purchased from Boehringer Mannheim (Smith et al, BioTechniques November/December:306–312, 1984). C-acetanilide (31.7 mCi/mmole) was bought from California Bionuclear.

Viruses and Cells: Vaccinia virus (strain WR), HeLa cells, CV1 cells, BSC-1 cells, and human TK$^-$ 143 cells were obtained from NIH, Bethesda, Md. The virus was grown in HeLa cells and purified from cytoplasmic extracts by sucrose density gradient centrifugation following the procedures described by Joklik (Virology 18:9–18, 1962). All cells were grown in Dulbecco modified Eagle's minimal essential medium containing 10% fetal bovine serum and TK$^-$ cells in addition had 25 µg of BrdUrd per ml.

Vectors and DNA: Coexpression insertion vector pSC-11 (Chakrabarti et al Mol. Cell. Biol. 5:3403–3409, 1985), and complementary DNA clones of cytochrome P1-450 and P3-450 (Kimura et al, J. Biol. Chem. 259,10705–10713, 1984) were employed in the construction of the recombinants. The plasmids were grown in bacteria and their DNAs purified by two sequential centrifugations on CsCl-EtBr equilibrium density gradients. DNA fragments were separated on agarose gels and purified by electroelution. Other recombinant DNA procedures were carried out by standard procedures (Maniatis et al, Molecular Cloning: A Laboratory Manual, Cold Spring Harbor: New York, 1982). Vaccinia virus DNA was extracted from the purified virions as described by Garon et al (Proc. Natl. Acad. Sci. USA 75:4865–4867, 1978).

Infection, Transfection and Isolation of Recombinant Viruses: The procedures were carried out essentially as described by B. Moss and colleagues (Mackett et al, J. Virol. 49:857–864, 1984; Smith, Supra.; Mackett et al, Proc. Natl. Acad. Sci. USA 79:7415–7419, 1982). Subconfluent CV-1 monkey kidney cells infected with wild type vaccinia virus (WT-VV) were transfected with 10 µg of recombination vector and 1 µg of wild type vaccinia virus DNA. Two days after incubation the recombinant TK$^-$ viruses formed within the cells were distinguished from the wild type by plaque assay on Tk$^-$ cells in the presence of BrdUrd (Chakrabarti et al, 1985 supra). The TK$^-$ cells with the TK$^-$ plaques were overlaid with agar containing 400 µg X-gal per ml to check for the concomitant expression of β-galactosidase and also to distinguish TK$^-$ recombinants from TK$^-$ mutants. The TK$^-$, β-gal$^+$recombinants were purified by two cycles of selection. The recombinants were then screened for the presence of P1-450 and P3-450 cDNA inserts by dot blot hybridization (Macket et al, 1982, supra.) and the virus stocks prepared in HeLa cells.

Protein Analysis by Immunoblotting: Cells were harvested by scraping and the lysates were prepared by three freeze-thaw cycles and brief sonication in a buffer containing 0.02 M Tris-HCl pH 7.5+0.25 M sucrose. Protein concentration was determined by Lowry's method (Lowry et al, J. Bio. Chem. 193:265–275, 1951). Electrophoresis in 7.5% polyacrylamide gels in the presence of NaDodSo$_4$ was performed as described by Laemmli (Nature 227:680–685, 1970). Prestained protein molecular weight standards (Bethesda, Research Laboratories) were used to estimate the size of the polypeptides. The electrophoresed proteins were transferred to nitrocellulose membranes and the transferred proteins detected by Western blotting (Towbin et al, Proc. Natl. Acad. Sci. USA 76:4350–4354, 1979) using a mixture of rabbit antisera against P-450c and P-450d. The P-450c and the P-450d forms are the rat homologues of mouse P1-450 and P3-450, respectively. These proteins share a high degree of homology and their antisera cross-react with each other. The immunoblots were detected by incubating with goat anti-rabbit immunoglobulin G conjugated with alkaline phosphatase (KPL Labs, Gaithersburg, Md.) in conjunction with the chromogenic substrate 5-bromo-4-chloro-3-indolyl phosphate/p-nitro blue tetrazolium chloride.

Measurement of Co-Reduced Difference Spectra: Microsomal fractions were prepared from the cell lysates. The lysates were centrifuged at about 700 g for 10 minutes and the supernant was recentrifuged at about 8,000 g for 10 min. The resulting 8,000 g supernatant was centrifuged again at about 100,000 g for 60 minutes to pellet the microsomes. The microsomal fraction was suspended in 0.11M potassium phosphate buffer pH 7.5 containing 20% glycerol. For difference spectra the microsomal fraction was solubilized with 0.14% emulgen 913 (15 minutes), centrifuged at 100,000 g for 60 minutes and the supernatant used. The spectra were measured in an Aminco Instruments Company model DW-2a spectrophotometer as described by Omura et al (J. Biol. Chem. 239:2370–2378, 1964).

Enzyme Assays: Aryl hydrocarbon hydroxylase (AHH) activity was determined by measurement of the fluorescence of phenolic metabolites formed from benzo(a)pyrene (Nebert et al, J. Biol. Chem. 243:6242–6249, 1968). The reaction mixture contained in 1.0 ml: 50 µmol Tris-HCl pH 7.5, 0.3 µmol MgCl$_2$; 0.6 µmol NADPH; 100 nmol benzo(a)pyrene and 400 µg of cell homogenate. AHH activity is expressed as pmols of product equivalent to 3-OH benzo(a)pyrene formed per mg protein per min. Acetanilide hydroxylase activity was determined by measuring the conversion of $^{14}$-C acetanilide to its hydroxylated derivatives. The substrate and its metabolites were separated by silica gel thin layer chromatography (TLC) following standard procedures. The assay was carried out in a final volume of 1.0 ml containing: 50 umol Tris-HCl pH 7.5, 0.3 umol MgCl$_2$, 0.6 µmol NADPH, 2 µmol $^{14}$C-acetanilide at a specific activity of 1.0 m Ci/m mole and 500 µg of total cell homogenate. The enzyme activity is expressed as picomoles of product formed per mg of protein/min. An aliquot of the reaction product in methanol was spotted on 250 µ thin-layer silica gel plate (Whatman) and eluted with 95% chloroform +5% methanol. The Rf values for acetanilide and 4-hydroxy acetanilide under these conditions is about 0.74 and 0.2, respectively. The gel plate was autoradiographed and product quantified by counting the radioactivity after scraping from plate.

Figure 1:
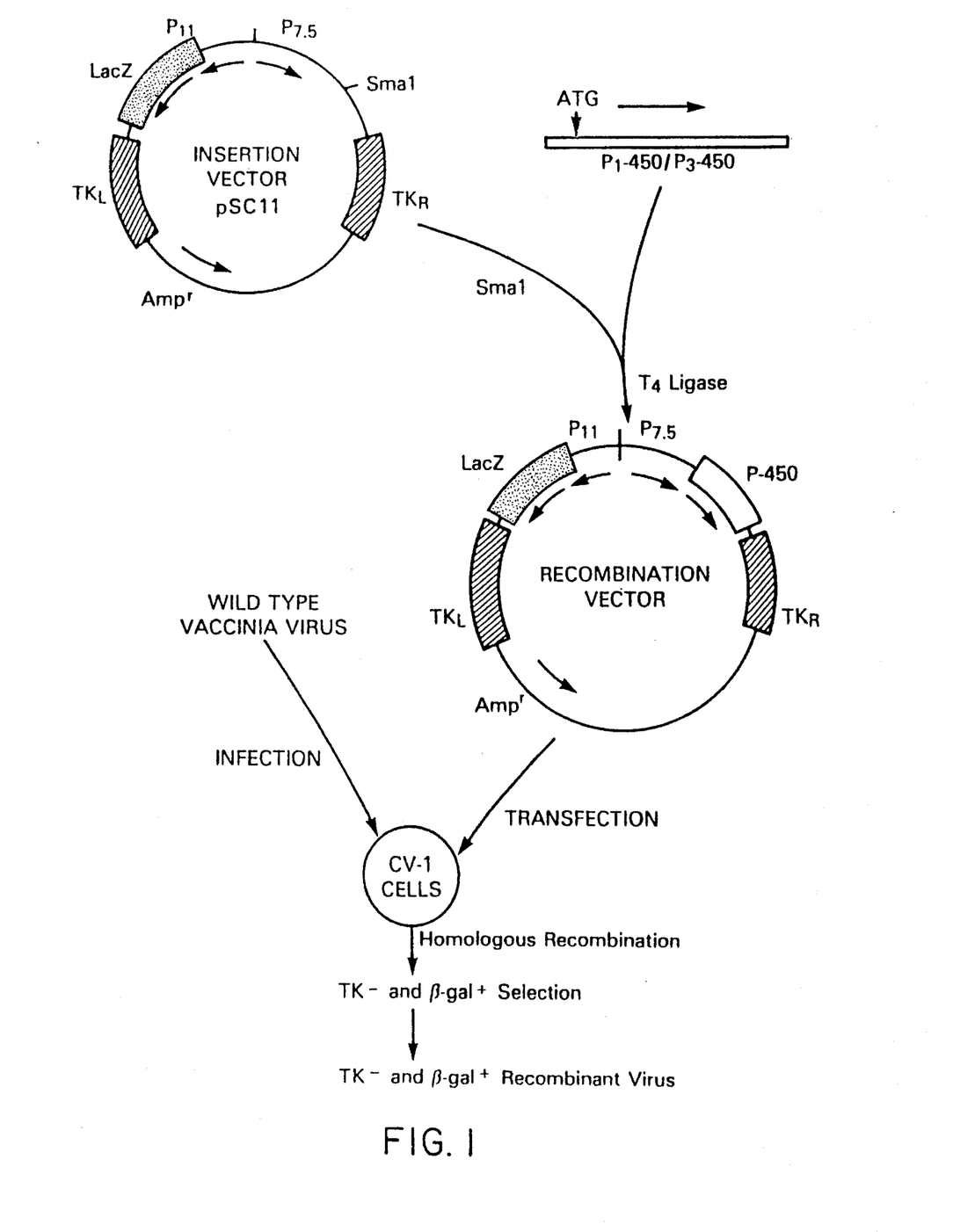
FIG. 1 shows schematic construction of recombinant vaccinia viruses for expressing mouse cytochromes P1-450 and P3-450. P11 and P7.5, vaccinia transcriptional regulatory sequences for 11K and 7.5K polypeptides respectively, Lac Z, *Escherichia Coli* β-galactosidase gene, $TK_L$, and $TK_R$, split segments of vaccinia virus DNA from left and right positions of TK gene respectively. $Amp^r$ is ampicillin resistance gene.

Construction of Plasmids and Virus Recombinants: Construction of the chimeric genes containing the transcriptional regulatory signals and RNA start site of vaccinia virus genes, the translational start site of the coding sequences of the mouse P1-450 and P3-450, and the incorporation of these sequences into the wild type vaccinia virus to form recombinants, are diagramatically presented in FIG. 1. The starting plasmid in the construction sequence of generating the recombinant virus is the insertion vector pSC-11. This coexpression insertion vector contains: the Escherichia coli β-galactosidase gene under the control of vaccinia promoter for 11K protein, a second promoter for 7.5K protein for transcription of coding sequences, a unique Sma 1 site down stream of the 7.5K promoter for the insertion of foreign protein coding sequences and flanking vaccinia virus TK sequences for homologous recombination inside infected cells (Macket, et al, 1984, supra.). A 2.6 Kb full-length cDNA for cytochrome P1-450 and 1.9 kb full-length cDNA for cytochrome P3-450 (Kimura et al, 1984, supra.) were modified and inserted into the unique Sma 1 site of the insertion plasmid to form the recombination vectors containing the individual P1-450 and P3-450. Selection of the recombination plasmids containing the P1-450 and P3-450 inserts in correct orientation was accomplished by restriction enzyme mapping. The two recombination plasmids were then individually used to transfect CV-1 cells previously infected with WT-VV. Homologous recombination between vaccinia TK sequences in the recombination plasmid and the virus genome resulted in insertion of the P-450 and the β-galactosidase sequences into the vaccinia virus. The progeny viruses were then plaque assayed on TK$^-$ cells in the presence of BrdUrd to select for TK$^-$ virus and overlaid with agar containing X-gal (chromogenic substrate for β-galactosidase) to select for β-gal$^+$ virus. The presence of the P1-450 and P3-450 inserts in the TK$^-$ and β-gal$^+$ recombinants was confirmed by dot blot hybridization (Mackett et al, *Proc. Natl. Acad. Sci. USA* 79:7415–7419, 1982). After two sequential plaque purifications the recombinant virus stocks were designated VV-P1 and VV-P3, respectively.

A deposit of the recombinant vaccinia virus containing the entire coding sequence for the P1-450 and P3-450 been made at the ATCC, Rockville, Maryland on May 29, 1987, under the accession numbers VR-2168 and VR-2169 respectively. The deposits shall be viably maintained, replacing if it became non-viable, for a period of 30 years from the date of the deposit, or for 5 years from the last date of request for a sample of the deposit, whichever is longer, and made available to the public without restriction in accordance with the provisions of the law. The Commissioner of Patents and Trademarks, upon request, shall have access to the deposit.

Figure 2A:
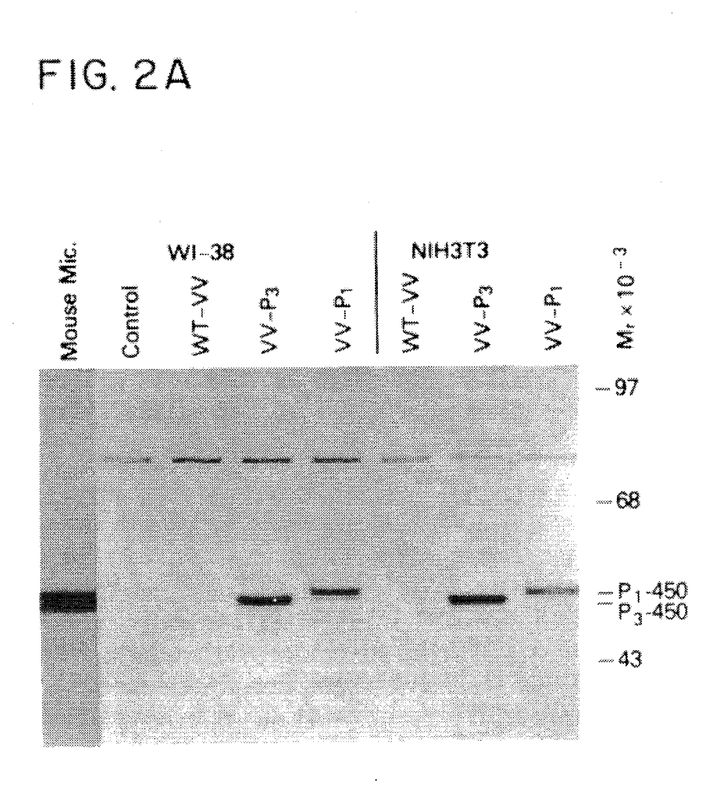
Figure 2B:
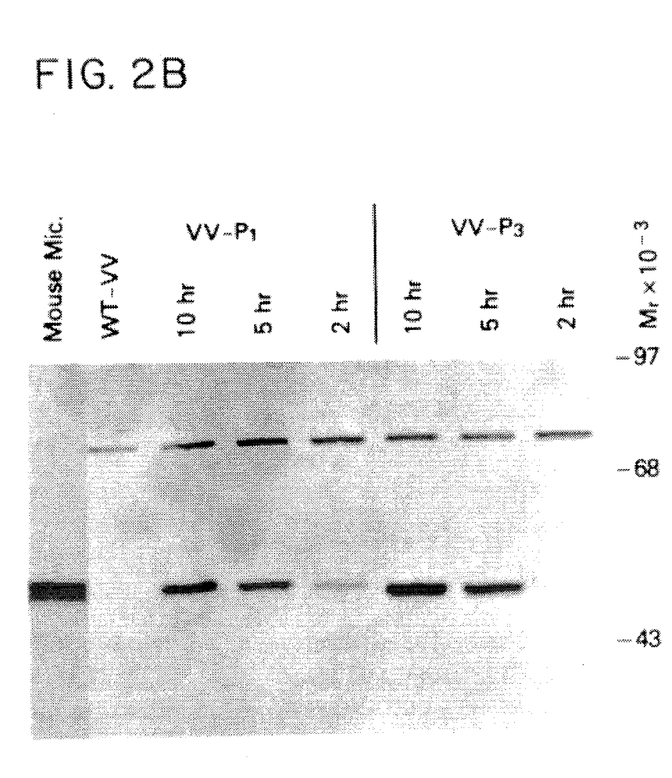

Analysis of P1-450 and P3-450 proteins in VV-P1 and VV-P3 Infected Cells: Lysates of human and mouse cells infected with each of the recombinant viruses were electrophoresed on NaDodSo$_4$-polyacrylamide gels and analyzed by immunoblotting (FIG. 2A). Both human WI-38 cells and mouse NIH 3T3 cells infected with the recombinant virus VV-P1 showed a peptide band which cochromatographed with P1-450 of mouse liver microsomes at M$_r$≈55,000. These same cells infected with the recombinant virus VV-P3 showed a slightly faster migrating protein band that cochromatographed with P3-450 of mouse liver microsomes at M$_r$≈54,000. In lysates of uninfected control cells or cells infected with WT-VV, neither the P1-450 nor the P3-450 bands were detected. The time course of synthesis of P1-450 and P3-450 in virus infected 3T3 cells is shown in the immunoblots in FIG. 2B. Cytochrome P1-450 and P3-450 were detected as early as 2 hours after infection and the amount of the expression product increased during subsequent 15 hour time interval. Based on the relative intensities of protein bands of P1-450 and P3-450 found in infected human and mouse cells and the P-450 contents of the mouse liver microsomes the specific content is estimated to be in the range of about 15–90 pmoles per mg of infected cells lysates. These results clearly show that the infectious vaccinia virus recombinants directed the synthesis of cytochrome P1-450 and P3-450 . The polypeptide products formed were indistinguishable from the native P1-450 and P3-450 of mouse microsomes. The synthesis of the correct size P1-450 and P3-450 polypeptides indicates that no fusion polypeptides were formed nor were any incorrect reading frames expressed. The detection of P-450 expression products at an early time after infection is consistent with the use of early vaccinia promoter.

Figure 3:
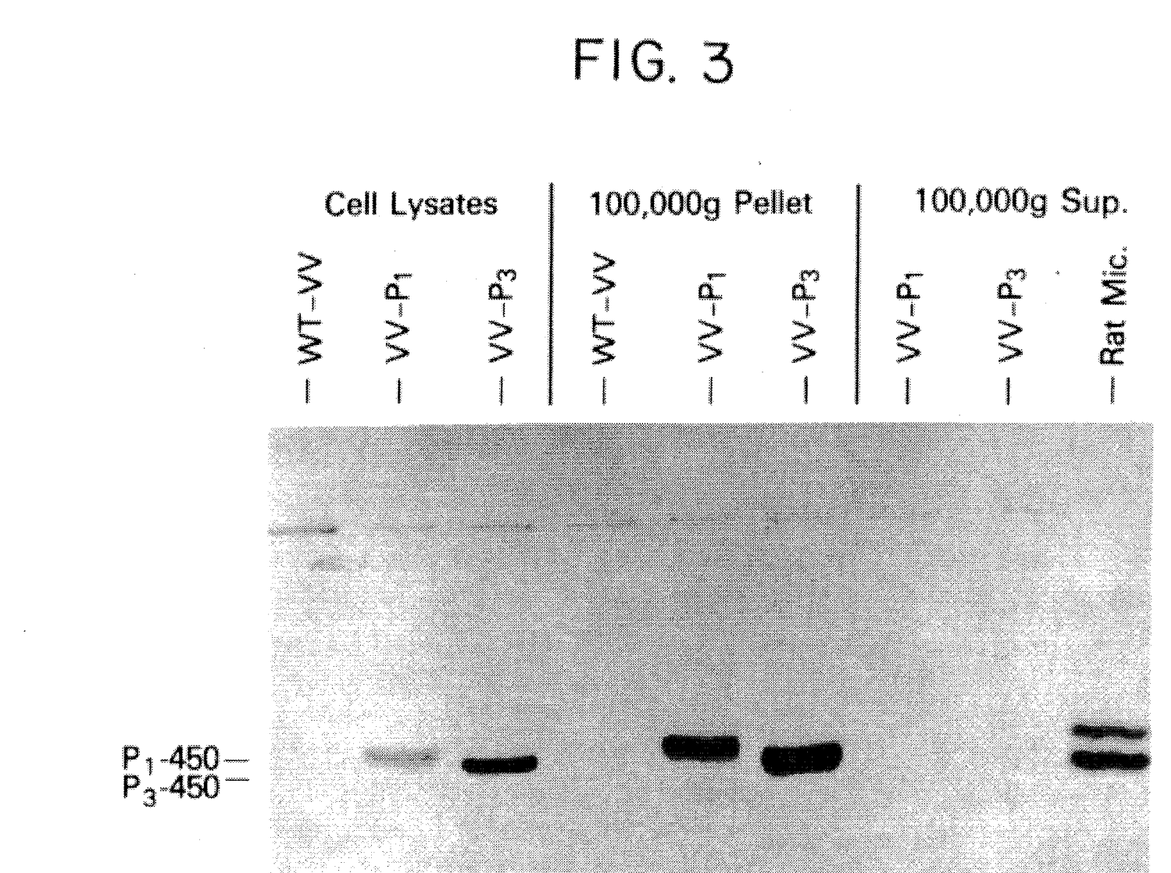
FIG. 3 shows cytochrome P1-450 and P3-450 polypeptides in subcellular fractions. In each lane 100 ug of protein was electrophoresed and immunoblotted.

Subcellular Localization of the Newly Synthesized P1-450 and P3-450: Native cellular P-450 apoproteins normally complex with heme to form hemoproteins which are subsequently transported to microsomal membranes. Therefore, it needed to be determined whether the newly expressed P1-450 and P3-450 likewise are transported to the microsomes in the cell. Hence, the distribution of P1-450 and P3-450 polypeptides in different subcellular fractions of VV-P1 and VV-P3 infected cells was determined by immunoblotting. Results presented in FIG. 3 show that the newly expressed cytochrome P-450s were concentrated in the microsomal fraction (100,000 g pellet). Either none or neglegible amounts were detected in the 100,000 g supernatant. These results indicated that the cytochrome P-450s synthesized by recombinant vaccinia viruses VV-P1 and VV-P3 are translocated to the microsomal membranes. Comparison of the relative band intensities of infected cells lysates and microsomes indicated a ten-fold enrichment of the expressed P-450s in the microsomal fraction.

Figure 4:
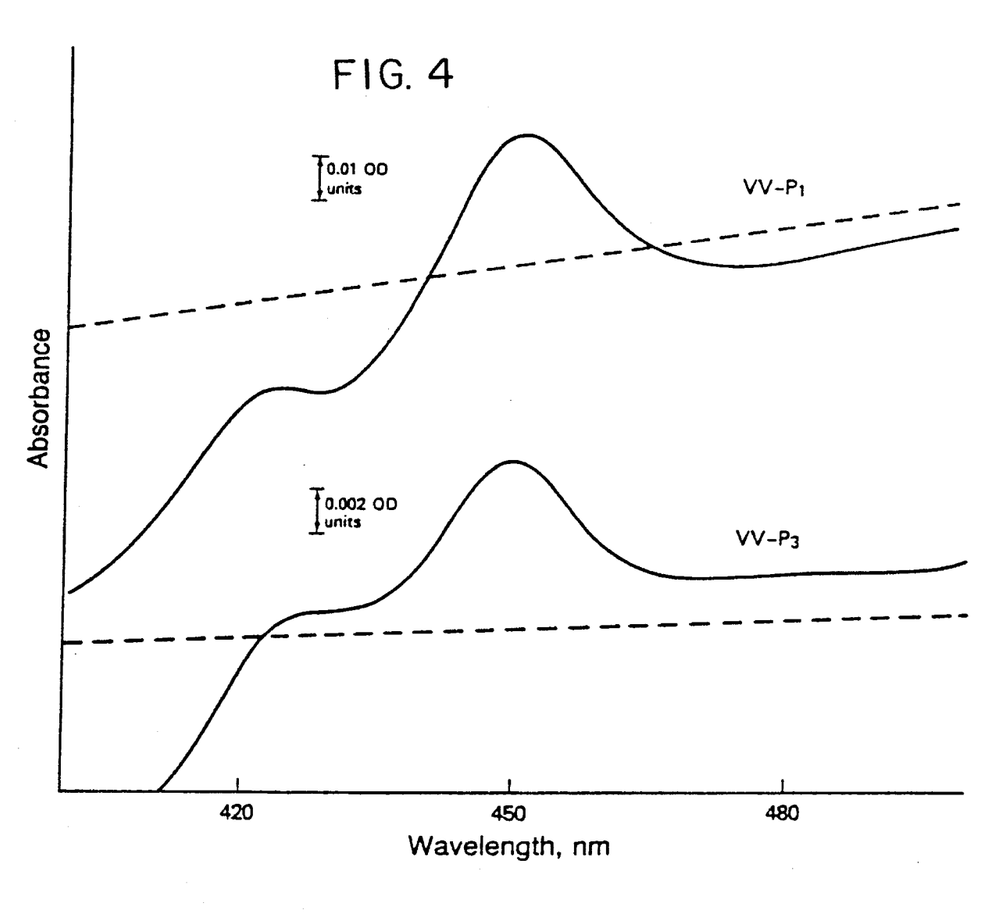
FIG. 4 shows the CO difference spectra of dithionite reduced microsomal fractions. Microsomes were solubilized with emulgen 913 and the supernatant used for spectra.—dithionite reduced spectra,—reduced and CO saturated spectra.

Spectral Characterization of Cytochromes P1-450 and P3-450: A characteristic feature of microsomal cytochrome P-450 hemoproteins is that the native catalytically active forms exhibit absorption maxima of reduced CO complex at 450 nm and the denatured catalytically inactive forms exhibit absorption maxima around 420 nm. Examination of the microsomal fraction of NIH 3T3 cells infected with VV-P1 showed an absorption maxima of reduced CO complex at 450 nm indicating that the newly expressed cytochrome P1-450 in microsomes is in native configuration (FIG. 4). Similarly, the microsomal fraction of cells infected with VV-P3 showed a 450 run Peak characteristic of native P-450. The specific content of cytochrome P1-450 was 0.028 ng per mg and P3-450 was 0.033 ng per mg of detergent-solubilized microsomal fraction. These results indicate that the cytochrome P1-450 and P3-450 proteins synthesized in virus infected cells incorporate a heme moiety, and are transported and sequestered into the microsomal fraction, in a manner indistinguishable from the native in vivo processed cellular P-450s.

Figure 5:
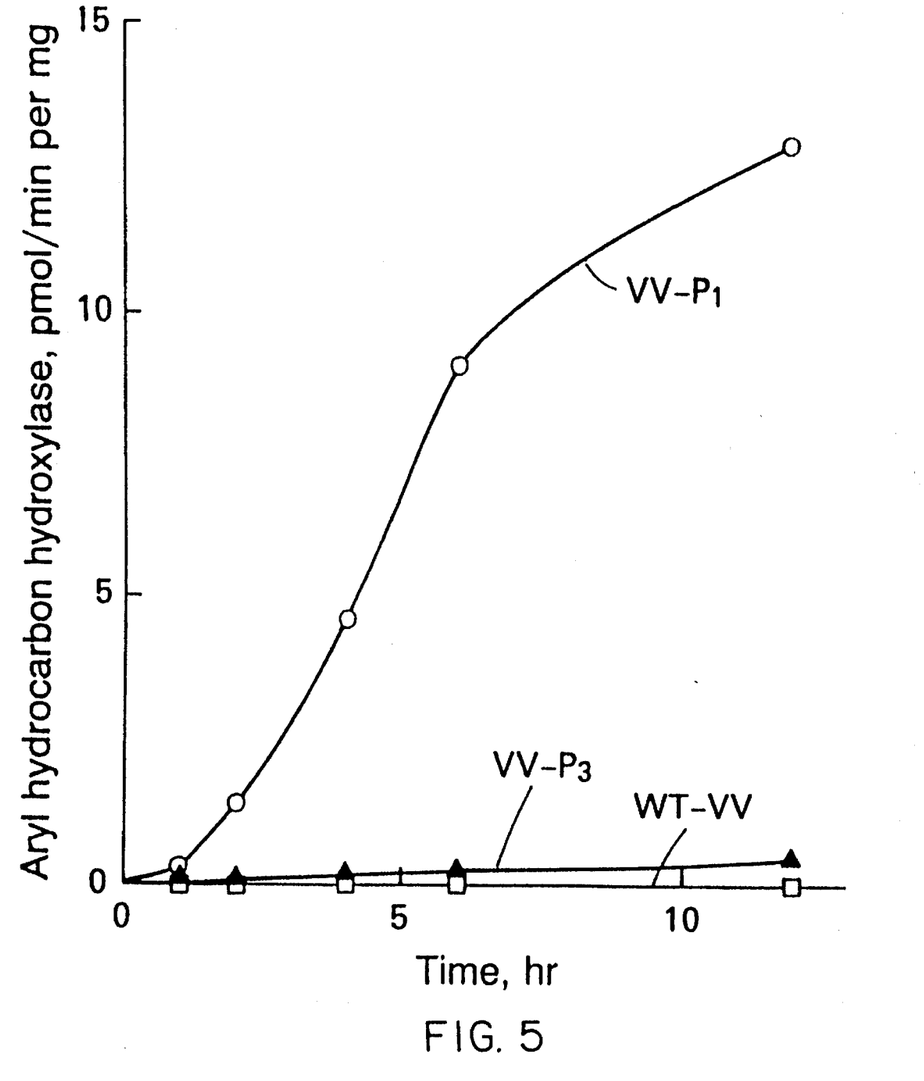
FIG. 5 shows the expression of AHH activity. Infected cells were harvested at the indicated time intervals and lysates assayed for AHH activity. NIH 3T3 cells infected with 0-0, VV-P1, VV-P3, WT-VV. No detectable activity was found in uninfected control cells (not shown)

Enzyme Activity of P-450s in W-P1 and VV-P3 Infected Cells: AHH activity in lysates of 3T3 cells infected with VV-P1 shows (FIG. 5) detectable enzyme activity as early as 1 hour after infection and an increase in the enzyme activity for 12 hours thereafter. However, the lysates of cells infected with VV-P3 showed only a small fraction of activity compared to that of VV-P1 even at 12 hours after infection. No detectable activity was found in uninfected control cells or in WT-VV infected cells. The AHH activity was completely inhibited by antisera against P-450c and P-450d (data not shown). The specific AHH activity in different preparations varied in the range of about 10–70 p moles per mg of cell lysates. .The AHH activity was at least 30-fold greater with P1-450 than with P3-450.

Figure 6:
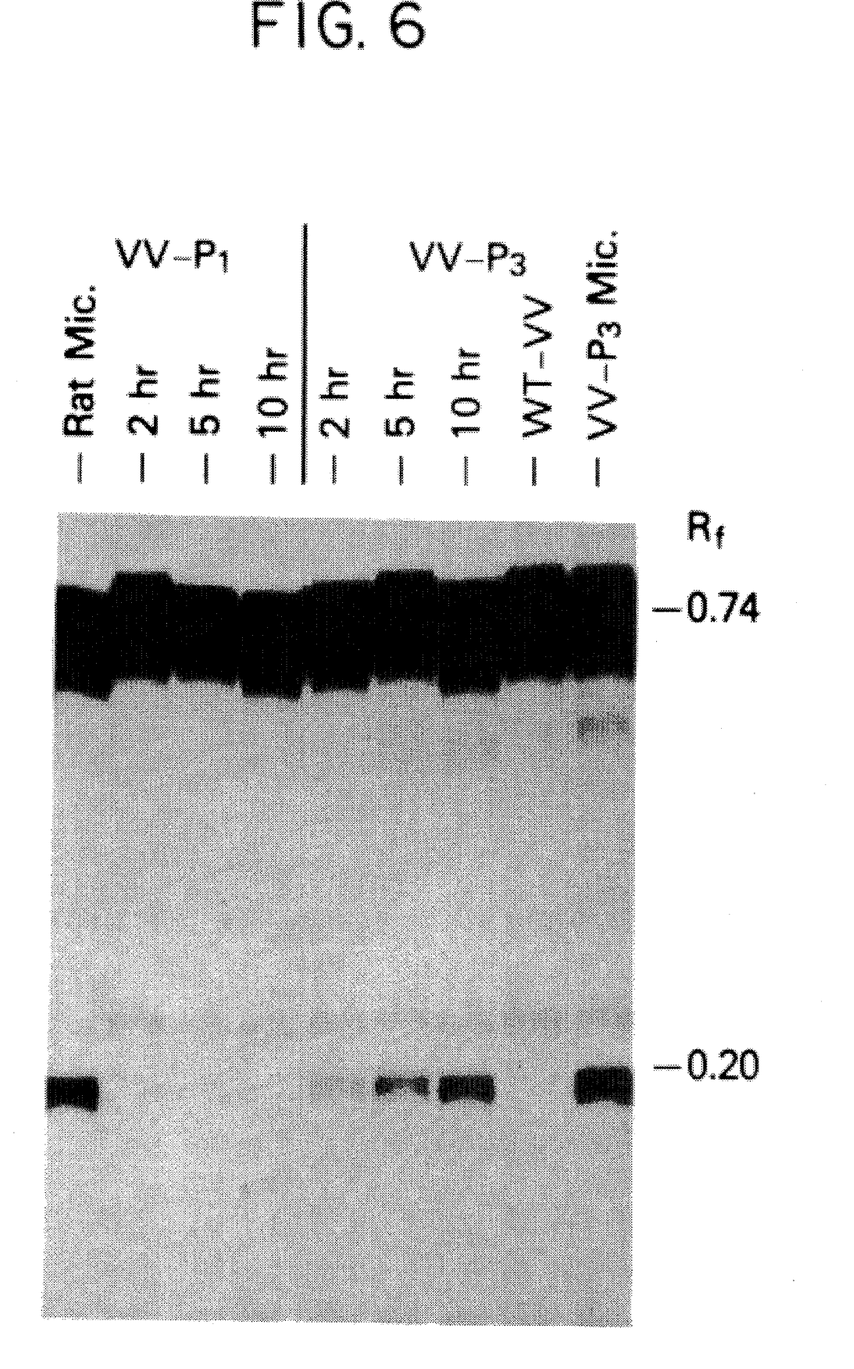
FIG. 6 shows TLC analysis of acetanilide hydroxylase activity. Cell lysates (500 µg) were assayed and the products separated by TLC.

Lysates of 3T3 cells infected with VV-P1 and VV-P3 for different time intervals were assayed for acetanilide hydroxylase activity and the autoradiograms of TLC analysis of the products formed are presented in FIG. 6. Lysates of cells infected with VV-P3, in addition to the intense substrate band ( Rf value of 0.74 ), showed a slow moving band (Rf value of 0.2) identifying the TLC migration position of the hydroxylated products of acetanilide. The formation of hydroxylated metabolites increased with time. In cells infected with VV-P1, however, there was no detectable band at an Rf value of 0.2. No activity was detectable in the control uninfected cells or in cells infected with WT-VV. A minor band at an Rf value of 0.12 was detected in Hepa 1 cells infected with VV-P1 after prolonged exposure result not shown). The specific acetanilide hydroxylase activity was about 45 pmoles mg of cell lysate. The acetanilide hydroxylase activity was at least 20-fold greater with P3-450 than with P1-450.

The assembly of the holoenzyme and expression of enzyme activity without the necessity of extraneous addition of any coenzyme or cofactor and the like, clearly show that the P1-450 and P3-450 proteins encoded by recombinant virus infected cells are synthesized as a complete catalytically active molecule. In contrast, it should be noted that P-450 cytochromes prepared by conventional means do not exhibit enzyme activity unless NADPH cytochrome P450 reductase and other cell fractions are extraneously added (Goldstein, et al, J. Biol. Chem. 257:2702–2702, 1982; Guengerich et al, Biochem. 21:6019–6030, 1982; Negishi et al, J. Biol. Chem. 254:11015–11023, 1979). Moreover, the cytochrome P1-450 of the present invention has 30–40 fold higher AHH activity than P3-450 and cytochrome P3-450 showed a 20-fold high acetanilide hydroxylase activity than P1-450, a characteristic and distinguishing feature of these two enzymes. Cells infected with recombinant viruses expressed $10^7$–$10^8$ molecules of the newly synthesized cytochromes per cell and this represents 0.1–1.0% of total cellular proteins.

The availability of functionally intact, pure P1-450 and P3-450 enzyme in accordance with the present invention now makes it possible for the first time to test in vitro the metabolism, detoxification, mutagenesis or activation of xenobiotic and endobiotic substrates. Availability of such a pure enzymatic system significantly facilitates the testing and development of new drugs, testing carcinogen metabolism, environmental chemical mutagens and the like without resorting to expensive and the time consuming in vivo systems. Furthermore, the recombinant vaccinia virus expression system of the present invention provides an easy, efficient and economical method of producing large quantities of pure catalytically active cytochrome P-450 enzymes which was not heretofore possible. To obtain pure P1-450 or P3-450 enzyme, mammalian or other suitable cells are simply infected with recombinant vaccinia virus of the present invention and the infected cells are used directly as a source of P1-450 or P3-450 enzyme which are synthesized as a result of the infection. Alternatively, the microsomal or endoplasmic reticulum fraction of the transfected cells can be separated and used as a source of the pure enzyme. The enzyme can also be linked to a mutagen detection assay such as the Ames salmonella/microsome system for detecting or testing the mutagenic frequency induced by environmental pollutants, carcinogens and the like (Ames et al, *Mut. Res.* 31:347, 1975). Other standard methods well known in the art such as chromosome aberration and sister chromatid exchange induction in Chinese hamster ovary cells (Galloway et al, *Environ. Mutagen.* 7:1, 1985) or mouse lymphoma cell mutagenesis assays (Myhr et al, *Prog. in Mut. Res.* 5:555–568, 1985) can, of course, also be used for testing mutagenicity.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. Mammalian cells infected with a vaccinia virus containing a DNA sequence coding for a cytochrome P-450 polypeptide in a manner allowing expression of a recombinant, functional cytochrome P-450 polypeptide.

2. The mammalian cells of claim 1, which express the cytochrome P1-450 polypeptide.

3. The mammalian cells of claim 1, which express the cytochrome P3-450 polypeptide.

4. A cell lysate of cultured mammalian cells, said cells having been infected with a vaccinia virus containing a DNA sequence coding for a P-450 polypeptide in a manner allowing expression of a recombinant, functional cytochrome P-450 polypeptide.

5. The cell lysate of claim 4 comprising a recombinant, functional cytochrome P1-450 polypeptide.

6. The cell lysate of claim 4 comprising a recombinant, functional cytochrome P3-450 polypeptide.

7. An isolated microsomal fraction of cultured mammalian cells, said cells having been infected with a vaccinia virus containing a DNA sequence coding for a cytochrome P450 polypeptide in a manner allowing expression of a recombinant, functional cytochrome P-450 polypeptide.

8. The fraction of claim 7 comprising a recombinant, functional cytochrome P1-450 polypeptide.

9. The fraction of claim 7 comprising a recombinant, functional cytochrome P3-450 polypeptide.

* * * * *